US008999395B2

(12) United States Patent
Zanichelli et al.

(10) Patent No.: US 8,999,395 B2
(45) Date of Patent: Apr. 7, 2015

(54) PHARMACEUTICAL COMPOSITIONS FOR ORAL ADMINISTRATION IN THE FORM OF STABILISED AQUEOUS SUSPENSIONS

(75) Inventors: Claudio Zanichelli, Sorbolo (IT); Simona Binacchi, Suzzara (IT); Sandrine Lacoste, Carignan de Bordeaux (FR); Cecilia Sacchetti, Reggio Emilia (IT)

(73) Assignee: Ceva Sante Animale, Libourne (FR)

( * ) Notice: Subject to any disclaimer, the term of this patent is extended or adjusted under 35 U.S.C. 154(b) by 1194 days.

(21) Appl. No.: 12/029,126

(22) Filed: Feb. 11, 2008

(65) Prior Publication Data

US 2008/0193548 A1 Aug. 14, 2008

Related U.S. Application Data

(60) Provisional application No. 60/889,161, filed on Feb. 9, 2007.

(51) Int. Cl.
*A61K 9/10* (2006.01)
*A61K 9/00* (2006.01)

(52) U.S. Cl.
CPC .................................. *A61K 9/0095* (2013.01)

(58) Field of Classification Search
None
See application file for complete search history.

(56) References Cited

U.S. PATENT DOCUMENTS

| 4,594,359 | A | * | 6/1986 | Padfield et al. ............... 514/647 |
| 4,996,222 | A | | 2/1991 | Carlin et al. |
| 5,112,604 | A | * | 5/1992 | Beaurline et al. ............. 424/490 |
| 5,688,529 | A | | 11/1997 | Lidgate et al. |
| 6,027,746 | A | | 2/2000 | Lech |
| 6,184,220 | B1 | * | 2/2001 | Turck et al. ................ 514/226.5 |
| 2004/0121966 | A1 | * | 6/2004 | Li et al. ............................ 514/28 |
| 2005/0288280 | A1 | * | 12/2005 | Friton et al. ............... 514/226.5 |
| 2007/0281927 | A1 | * | 12/2007 | Tyavanagimatt et al. .. 514/226.5 |
| 2008/0274196 | A1 | * | 11/2008 | Jayanthi et al. ............... 424/489 |

FOREIGN PATENT DOCUMENTS

| EP | 843 998 | 2/2002 |
| EP | 1 795 197 | 6/2007 |
| FR | 2 730 163 | 8/1996 |
| WO | WO 96/01628 | 2/1991 |
| WO | WO 93/21923 | 11/1993 |
| WO | WO 01/72284 | 10/2001 |
| WO | WO 2006/061351 | 6/2006 |
| WO | WO 2007/017905 | 2/2007 |

OTHER PUBLICATIONS

CAS Registry Record for 71125-38-7. Entered STN Nov. 16, 1984. 4 pages.*
PCT International Search Report for CEVA Sante Animale et al., Int'l Application No. PCT/EP2008/050492, filed Jan. 17, 2008, Dated Mar. 17, 2008.
French Preliminary Search Report for CEVA Sante Animale, French application No. 07/03530, filed Jan. 18, 2007, dated Aug. 16, 2007. (w/ English translation).

* cited by examiner

*Primary Examiner* — Robert A Wax
*Assistant Examiner* — Danah Al-Awadi
(74) *Attorney, Agent, or Firm* — Saliwanchik, Lloyd & Eisenschenk

(57) ABSTRACT

The invention relates to a liquid pharmaceutical composition, in the form of a suspension of micronized powder of active substance in an acceptable physiological liquid medium, stabilized over time, for administration via the oral route.

12 Claims, No Drawings

PHARMACEUTICAL COMPOSITIONS FOR ORAL ADMINISTRATION IN THE FORM OF STABILISED AQUEOUS SUSPENSIONS

This application claims benefit of US Provisional Application No. 60/889,161 filed Feb. 9, 2007, the entire disclosure of which is incorporated by reference herein in its entirety.

The present invention concerns new pharmaceutical compositions intended for administration via the oral route in the form of stable aqueous suspensions of micronized powder of one or more active substances.

Oral administration of drugs is one of the preferred routes for treatment, because of its simplicity. While drugs are generally administered in the form of tablets, administration of tablets may be less preferred, for example when the dosage has to be finely adapted to treated subject, or may be less convenient, for example in the case of paediatric or veterinary drugs, where it is difficult to have a tablet swallowed, in the case of children, animals and individuals with an inflammated throat. The liquid form then turns out to be more appropriate as an alternative. However, a non soluble active substance requires solubilisation in a dispersion medium with a good appetence. An aqueous medium is a choice medium to disperse the active substance powder and obtain a suspension which can easily be orally administered (low viscosity, neutral taste, absence of intrinsic toxicity.

Preparation of aqueous suspensions from powders presents difficulties which are often tricky to overcome, such as colloidal stability of the suspension. Sedimentation of the suspension should be avoided as much as possible and if sedimentation appears, restoration of the suspension must be as rapid as possible by simply shaking the vial by hand. Otherwise, the risk of a dosage error during use may be high, which is unacceptable for a drug. Furthermore, the suspension is often dispensed using a dropper or a dispensing syringe, thereby requiring liquid suspensions which are able to flow freely from the dispensing devices. In addition, it is preferable for practical reasons to avoid the solution excessively wetting the walls of the container and the dispensing device, in order to avoid that large quantities remain on the device walls (poor dosage, loss of product, etc.). Finally, foaming of the product should be avoided, which would make dosage imprecise and uncertain.

Anti-inflammatory substances are among the drugs which may benefit from a presentation in a liquid form. Their dosages must be precise, e.g., dependent on the weight of the treated subject. If administered to subjects presenting inflammation of the upper oral sphere, these may be difficult to swallow in a solid form. On the other hand, the majority of anti-inflammatory molecules have poor solubility in water. Preparation of an aqueous liquid form of anti-inflammatory compounds therefore requires preparation of a stabilised aqueous suspension based on micronized powder of an anti-inflammatory active substance. Such anti-inflammatory molecules or compounds include for example non-steroidal anti-inflammatory compounds (NSAIDs).

Several strategies are known to the skilled person in order to obtain this type of suspensions or dispersions of stable powders. It is well known that a suspension of powder in a liquid is thermodynamically unstable and only the kinetics of the sedimentation can be modified. Pseudo-stability is therefore always involved. Four parameters may affect the sedimentation rate, e.g., the size profile of the powder, the difference in density between the powder and the dispersion medium, the interactions between particles, and the viscosity of the dispersion medium.

The size specifications of a powder are generally provided as a proportion below a size threshold of the particles. For example, a stable suspension of an anti-inflammatory substance such as the meloxicam may be described as being obtained from the active substance with at least 90% of the particles with a size of less than 50 μm. Such approach however, is somewhat simplistic, and may be disappointing. Additional parameters have to be taken into consideration. First, particle size affects the sedimentation rate via the effect of Brownian motion, which is all the more effective when the particles are fine. Other phenomena should be considered, and more particularly the depletion interactions (Bibette J. et al, Phys. Rev. Lett. 65, 2470-2473 (1990)), which occur as soon as the particle population is no longer homogenous and in particular if it is bimodal. It is therefore preferable to specify the size profile of the particle population, rather than a simple threshold value or a mean. In addition, the shape of the particles should be taken into account. Interactions between particles are generally different depending on whether the particles are spheroid or present marked anisotropy. Often, failure to take account of the shape of the particles results in incorrect profile measurements, particularly if one uses a light scattering method, since the intensity diffused by a particle depends among other aspects on the form factor.

The sedimentation rate also depends on the difference in density between the powder particles and the dispersion medium. While it is generally difficult to adapt the density of the active substance, the density of the dispersion medium may be modified to be closer to that of the powder. This can be obtained for example by dissolving solutes, when it is preferred not to basically change the dispersion medium. The limitations then lie in the pharmaceutical acceptability of these solutions, in terms of taste, which may become for instance rather salty.

Particles in suspension interact with the solvent and with each other. If the particles are small enough, these interactions may play a role in the aggregation and flocculation phenomena, thereby affecting sedimentation. This is particularly true in the case of electrostatic interactions which have a greater impact than Van der Waals interactions. The presence of electrolytes in the solution may limit the electrostatic interactions and therefore reduce any repulsive interactions. In practice, solubilisation of electrolytes may have a beneficial effect on the density, but may result in an aggregation phenomenon, which is undesirable.

The stability of the suspension also depends on interactions between the granules of powder and the dispersion medium. The wettability of the powder and the wetting characteristic of the medium will make it possible to modify the colloidal stability of the suspension. Although it is not always simple to alter the surface of the powder, the wetting characteristic of the medium may be modified by adding surfactants. However, several pitfalls may arise from the use of surfactants. If, for example surfactants with an excessively high detergent power are used, undesirable foaming effects are observed. The choice of the surfactant and its dosage are therefore critical and it is usually preferable to avoid addition of such compounds to pharmaceutical compositions.

Viscosity of the medium is the last adjustable parameter. An increased viscosity of the medium results in a reduced sedimentation rate. In this respect, U.S. Pat. No. 5,112,604 describes for example a suspension in the form of a syrup comprising a 1:1 mixture of 70% sorbitol and syrup as the suspension medium, microgranules with a controlled release of theophylline or salicylsalicylic acid having particles sizes of 125 μm, silicon dioxide, a polysaccharide gum, and a wetting agent or a mixture of wetting agents in order to modify the wettability of the microgranules. The addition in the dispersion medium of a mixture comprising a 1:1 mixture of sorbitol solution and syrup results in a substantial increase in the viscosity, which keeps the suspension stable and uniform with no sedimentation for about 90 days. However, an important increase in the viscosity is not always desirable, since the suspension must keep practical implementation characteristics for example for dosing using a dropper or a dispending device. In fact, an increased viscosity only reduces the sedimentation rate, but does not prevent sedimentation over time and makes re-suspension more difficult. In addition, the formulation as described in U.S. Pat. No. 5,112,604 requires the addition of surfactants such as simethicone to alter the surface tension parameters of the microgranules and thus makes it possible to improve interactions between the powder and the dispersion medium, This however causes foaming during manufacture and use and thus further requires adding anti-foam compounds. This solution is clearly not satisfactory from a pharmaceutical point of view and is preferably avoided since surfactants are frequently allergenic and/or irritant to the mucous membranes.

Alternatively, it has been proposed to modify the three-dimensional structure of the suspension in order to avoid phase separation and sedimentation phenomena. In this respect, U.S. Pat. No. 6,184,220 describes stable dispersions of micronized meloxicam in the presence of colloidal silica. However, the colloidal silica must be then dispersed under sufficient shear in order to create a so-called "siloid" three-dimensional structure, which traps the granules of active substance and prevents sedimentation. This three-dimensional siloid structure seems to act as an efficient stabilizer of the sedimentation over time since the volume of the three-dimensional structure only decreases by 20% after several months' storage with no sedimentation. However, a significant disadvantage of U.S. Pat. No. 6,184,220 compositions lies in the necessity to apply significant shearing forces, for the formation of a three-dimensional siloid network or structure. This step clearly renders the manufacture complex, and mostly batches are not reproducibly manufactured. In particular, from a pharmaceutical point of view, it appears difficult to assess formation of this particular three-dimensional structure, the only way being to assess the long terms stability from one batch to another, except after a longer time period of observation. In effect, characterisation of this three-dimensional structure, such as the dimension of the network and its symmetry, etc. . . . , seems to be difficult to measure, thereby making difficult the assessment of the quality and the reproducibility of pharmaceutical batches on an industrial scale.

It has been discovered that the use of specific selected natural polysaccharide polymers when used in combination with silicon dioxide, results in an excellent stabilisation over time of the suspensions for about 36 months at 20° C. Such stability is however obtained without requiring any additional step of dispersing the silicon oxide by application of shearing forces thereto in order to form a three-dimensional siloid network, and surprisingly does not require the addition of surfactants, either.

The specific polysaccharides polymers used according to the present invention do not present any modifications by addition of ether functions on the side chains, and are selected among carrageenans, xanthans, guars and alginic acid derivatives.

Particular combinations of such specific polysaccharides polymers and silicon oxide without formation of any three-dimensional siloid structure according to the present invention thus allows stabilizing suspensions of a micronized powder of anti-inflammatory active substance over time without affecting the viscosity of the suspension. As indicated above, using the specific polysaccharides gums according to the present invention makes it possible to avoid adding surfactants and anti-foaming compounds. In addition, polysaccharides gums according to the present invention are natural, and thus have an important advantage in terms of safety. Indeed, compounds which are obtained by chemical synthesis are more and more suspected to cause allergic reactions.

The present invention thus constitutes a major advance for the preparation of suspensions of micronized powder of active compounds, since it does not require any additional step of structuring the suspension in the form of a three-dimensional network by application of a shear thereto, and without having to add surfactants. On the contrary, the suspension according to the present invention is simply obtained by mixing and homogenizing the various ingredients while stirring and does not require any particular equipment, and does not require application of specific shear. In fact, the present invention results in the formation of reproducible pharmaceutical batches and may be easily controlled. Also, the suspension obtained according to the present invention remains homogeneous with no phase separation and no sedimentation during long periods of time of 18 months to 36 months at 20° C.

SUMMARY OF THE INVENTION

The present invention relates to a stable liquid pharmaceutical composition intended for oral administration comprising a suspension of a micronized powder of a pharmaceutical active substance dispersed in a physiological medium with about 0.01 to 1% by mass of a polysaccharide polymer selected from among the carrageenans, xanthans, guars and alginic acid derivatives. The viscosity of the suspension so obtained is less than 30 cp (centipoises) at 20° C. The aforementioned compositions may further comprise from about 0.1 to 5% or 0.1 to 2% by mass of a micronized powder of silicon oxide.

The compositions according to the present invention are particularly useful for formulating active substances having a low level of solubility, e.g., less than 500 mg/L in the dispersion medium at ambient temperature, in particular, non-steroidal anti-inflammatory compounds, such as enolcarboxamide acid derivatives, and more particularly meloxicam.

The compositions according to the present invention may also include conventional ingredients of pharmaceutical formulations, which are not essential in order to obtain the suspension according to the invention, such as preservatives or antimicrobial agents. Nevertheless, the pharmaceutical compositions according to the present invention do not require addition of surfactants or anti-foaming agents. Furthermore, they have taste and appetence characteristics such that it is not necessary to use any additional flavouring agent.

The present invention also relates to a process for preparing a stable aqueous suspension of micronized powder in which the colloidal stability is obtained by addition of about 0.01 to 1%, 0.1 to 1%, or 0.2 to 1% of a polysaccharide polymer selected among the carrageenans, xanthans, guars and alginic acid derivatives. The viscosity of the suspension so obtained is less than 30 cp (centipoises) at 20° C.

DETAILED DESCRIPTION OF THE INVENTION

The present invention thus consists of a liquid pharmaceutical composition, in the form of a stable suspension of micronized powder of an active substance in a liquid physiological medium acceptable for oral administration, and stabilised in order to prevent sedimentation over long storage periods of around 36 months at 20° C. The surprising effect is that colloidal stability is obtained by addition of a precise amount of a particular polysaccharide polymer while maintaining an acceptable viscosity of the suspension of less than 30 cP or between 18 and 30 cP (centipoises). Also, the present invention does not require structuring the suspension in the form of a three-dimensional network by application of a high shear when incorporating the micronized powder of metallic oxide to the suspension and does not require adding any surfactant compounds. The pharmaceutical compositions of the present invention are preferably free of surfactants.

Stable or stabilised suspension is intended to mean a composition the sedimentation rate of which is low enough to entail no sedimentation during storage, i.e., around 36 months. Sedimentation is detected by the occurrence of a phase separation. Sedimentation may be visualized by the formation of a light coloured ring on the surface of the suspension which progresses until two distinct phases are observed: a transparent phase and a charged phase. No phase separation or phase difference was observed during storage of pharmaceutical compositions according to the present invention. The pharmaceutical compositions according to the present invention are stable over time, throughout the shelf life of the drug, i.e., for long periods of time, e.g., approximately two to three years, or depending on the use of the product, ranging from a few weeks to several months, to at least about three years as shown in the Examples below.

The present invention is particularly useful for the preparation of suspensions of pharmaceutical active substances for which administration by tablets is undesirable or impractical. It particularly applies to active substances for which the dosage must be finely adapted to the patient, which may be obtained by means of an easily dosable liquid form. These involve for example paediatric and veterinary drugs for which the weight of the subject widely varies and for which administration of tablets is not very suitable.

The suspension according to the present invention obviously applies to pharmaceutical forms which are insoluble in the selected physiological dispersion medium. Indeed, solubility, even partial, of the active substance in the dispersion medium is liable to result in solubilisation followed by recristallisation as a function of the variations in temperature for example, and may modify the size profile of the powder grains, which is undesirable. In general, a solubility of less than 500 mg/L at ambient temperature is sufficiently low to avoid this phenomenon.

Colloidal stability is an essential quality criterion of the pharmaceutical product. It was observed that, following a large number of tests comparing different additives at different concentrations, excellent colloidal stability of the suspensions of micronized powders of pharmaceutical active substances could be obtained by adding precise quantities of particular polysaccharide polymers to the dispersion medium. The polysaccharides used for preparation of the stable suspensions of active substance powder are natural soluble polysaccharides unmodified by ether functions on the side chains. These polymers are well known in the art (ZATZ J L: Applications of gums in pharmaceutical and cosmetic suspensions. *Ind Eng Chem Prod Res Dev* 1984; 23:12-16; Bumphrey G: Extremely useful new suspending agent: *Pham J* 1986; 237:665). They belong to the classes of carrageenans, xanthans, guars and alginates. The xanthan gum class is preferred for achieving long-term colloidal stability for the suspensions according to the present invention. Mass to volume ratios of about 0.01% to 1% of the polysaccharide polymers are used.

In spite of the known viscosing effect of addition of polysaccharides, stabilisation of the suspension does not result from a significant increase in viscosity. Indeed, stable suspensions were obtained with viscosities not exceeding 30 cp (centipoises) and even generally as low as 18-30 cp (centipoises) at 20° C. The viscosity may be measured using well known methods in the art, for example with a rheoviscosimeter. More precisely, 2 ml of the pharmaceutical composition according to the present invention are placed in a space located between a flat disk and a cone, 60 mm in diameter. Viscosity of the composition is then determined by applying a force of 1000 to 2000s$^{-1}$ at 20° C.

However, as described in the Examples, hydrophilic polymers, such as cellulose ether derivatives which are commonly used to stabilise suspensions do not have the effect obtained with the polysaccharide polymers. Preferably, the compositions according to the present invention do not comprise any cellulose ether derivatives.

The pharmaceutical compositions according to the present invention also include micronized powders of metallic oxides, for example, of silicon, titanium or aluminium. Preferably, silicon oxide is used. Micronized powders of metallic oxides are added to the suspension of active substance and polysaccharide polymer by simple mixing and allow a more rapid homogenisation of the suspension without resorting to any significant shearing. The micronized powder of metallic oxide, such as a silicon oxide are dispersed via simple homogenisation and stirring at around 300-500 rpm. The compositions according to the present invention include about 0.1-5%, 0.1-2%, 0.5-2%, 1-2%, or 1.5-2% by mass of micronized powder of metallic oxide, preferably of silicon oxide. The silicon oxide has no three-dimensional siloid structure. Indeed, as described above, the silicon oxide according to the present invention is dispersed by simple homogenisation without applying high shear thereto in order to form a three-dimensional structure or network contrary to what is described inter alia in U.S. Pat. No. 6,184,220.

The pharmaceutical compositions according to the present invention are particularly useful for the preparation of oral forms of non-steroidal anti-inflammatory molecules (NSAIDs). Many molecules have been developed and used as NSAIDs. Representative classes of NSAIDs include, but are not limited to:

the propionic acid derivatives, e.g. ibuprofen, ketoprofen, carprofen, flurbiprofen, fenoprofen, fenbufen, etc. and salts thereof, the acetic acid derivatives, e.g. diclofenac, fenclofenac, indomethacin, ibufenac, etc. and salts thereof, the fenamic acid derivatives, e.g. nifluminic, mefenamic, meclofenamic, tolfenamic and flufenamic acids, and salts thereof, the enolcarboxamide derivatives, e.g. piroxicam, tenoxicam, lornoxicam and meloxicam, and salts thereof, and the acetylsalicylic acid and salts thereof.

These compounds are known to the skilled person who will be able to use them at the required dosage. Generally, these compounds require dosages on the order of 25 to 500 mg per administration for adults. The active substance concentration in the suspension which is the subject of the present invention may be adapted to supply a therapeutically sufficient dose of active substance in the present suspension for oral administration. The volume of the oral suspension is generally from 1 to 10 mL. In veterinary medicine, the dosage is generally given per kg of body weight of the animal. The dosage of these compounds varies from 0.1 mg/kg to 10 mg/kg. Since the volume to be administered is of the order of 1 to 10 mL, the pharmaceutical compositions according to the present invention may contain between 0.1 mg/mL and 10 mg/mL of the active substance, depending on the active substance and the treated animal.

These compounds are obtained in the pure state in powder form. The granulometric profile of the active substance powder may be adapted in order to obtain powders with a size profile that is homogenously unimodal and centered on a value of less than 10 μm, hereby avoiding interactions between particles of the depletion interaction type. Micronization is a conventional technology well known in the field of pharmacy (Rasenack N and Muller BW "Micron-size drug particles: common and novel micronization techniques", Pharm Dev Technol. 2004; 9(1):1-13). Preferably, the form factor is close to isotropy, or has an anisotropy factor of less than 2 (ratio of the lengths of the main axes). This may be readily observed by optical microscopy.

The dispersion media are well known to those skilled in the art. These media are selected according to their safety and acceptability in terms of taste and texture. They are generally physiological and inert media, i.e., they do not harm the chemical stability of the active substance, whether by hydrolysis or by oxidation or by any other form of degradation. For example, aqueous-based media such as water and demineralised water, with the addition of mixtures based on polyols may be used.

In the case of media having an aqueous base, the pH may be adjusted in order to avoid the solubilisation of the active substance, but also in order to avoid its degradation. Simple considerations of differences between chemistry in an homogenous medium and in an heterogeneous medium suggest to those skilled in the art that media in which the active substance is very sparingly soluble are less liable to degradation.

Since several of the active substances mentioned are acid derivatives, their solubility depends on the pH of the medium. This adjustment is well known in the field and may be obtained by using buffers acceptable for pharmaceutical applications via the oral route, such as for example phosphate, citrate, glycine, or borate buffers. For example, in one embodiment of the present invention, the compositions comprise meloxicam as the active substance and the pH may be adjusted to a pH of 2-4, 2-3 or 3-4, for example by adding a phosphate buffer, a citrate buffer, or a mixture thereof.

Other compounds may be further added to the compositions according to the present invention, among the compounds conventionally used to adapt the physical and chemical properties of the pharmaceutical compositions. For example, compounds which may improve the texture, guarantee microbial preservation, reduce the effects of oxidation and/or ensure chemical stability of the active substance and avoid its dissolution may be used. It is well known in the art to add to the medium non-ionic solutions or liquid such as sugar derivatives or polyols. Glucose, fructose, mannitol, sorbitol, or liquids such as glycerol or xylitol, etc. may be added to the suspensions. Polar liquids are generally added in proportions up to 50%, even 70% of the dispersion medium. Likewise, solutes may be added in proportions up to 20 to 30% by mass of the total mass.

The pharmaceutical compositions according to the invention have highly satisfactory appetence which is fully compatible with administration by the oral route and therefore do not require addition of a flavouring agent.

Furthermore, the compositions according to the present invention do not require any addition of surfactant agent and/or anti-foaming agent, which is an important additional advantage. They may therefore be free of surfactant agents and/or anti-foaming agents.

Pharmaceutical compositions according to the present invention which are administered orally may be stored and used for several days after opening and thus may also comprise compounds that would protect against growth of microbial flora, such as for example derivatives of formic, sorbic, benzoic, or propionic acids. Preferably, sodium benzoate is used in a low proportion, less than 1% or 0.1-1% by mass and is extremely safe.

In one preferred embodiment of the present invention, the stable pharmaceutical composition comprises meloxicam. Xanthan gum may then preferably be used as polysaccharide gum. Furthermore, the stable liquid composition of meloxicam includes micronized metallic oxide, particularly colloidal silica or silicon dioxide. The meloxicam compositions according to this embodiment may comprise other pharmaceutical ingredients intended to improve the texture, chemical stability and microbial preservation. In particular, the aqueous suspensions have pH of 2-4, 2-3, or 3-4, adjusted for example by a phosphate or citric buffer. Preferably, the compositions contain 0.05-1% of meloxicam, 0.01 to 1% of xanthan gum, 0.5 to 2% of colloidal silica, 0.1 to 1% of sodium benzoate as a preservative, glycerol, xylitol and sorbitol in an overall proportion of 50 to 70%, the proportions being expressed by mass percentages. Meloxicam may be used in proportions of 0.05-1%, 0.1-0.75%, 0.1-0.5%, 0.1-0.4%, 0.1-0.3%, 0.1-0.2%, and preferably in a proportion of 0.15%. Xanthan gum may be added in a proportion of 0.1-1%, 0.2-0.8%, 0.2-0.7%, 0.2-0.6%, 0.2-0.5%, 0.2-0.4%, or 0.2-0.3%, and preferably in a proportion of 0.25%. Despite the high proportions of xanthan used in the composition of the present invention, the viscosity of the composition remains stable over time, during up to 18 to 36 months at 20° C., and remains less than 50 cP, or less than 30 cP at 20° C. Colloidal silica may be added in a proportion of 0.5-2%, 1-2%, 1.5-2%, and preferably in a proportion of 2%. The preservative sodium benzoate may be used in a proportion of 0.1-0.8%, 0.1-0.6%, 0.1-0.4%, 0.1-0.2%, and preferably around 0.15%. It is remarkable that the quality of the suspension has a good appetence, and thus does not require addition of any flavouring agent, as is generally the case.

According to a preferred embodiment, stabilised pharmaceutical compositions comprise a stable suspension of meloxicam which is well known in the art for its therapeutic effects and is thus useful as a drug. The stable suspensions of meloxicam may be administered orally for example for treating subjects, such as non human mammals.

Furthermore, the present invention relates to a treatment method comprising administering a therapeutically effective dose of the above-described pharmaceutical compositions to a patient, such as a non human mammal.

Generally, in the animal therapy, the veterinary and/or farmer may easily determine the dosing depending on the disease, age, weight of the animals, and other parameters.

The oral compositions according to the present invention may be administered orally directly in the oral cavity of the animal or mixed with the food. Dosages may be performed via specific systems of delivery well known in the art.

In a second embodiment, the present invention also provides a process for preparing a stable suspension of micronized pharmaceutical powder, in which colloidal stability is obtained by addition of a small quantity of particular polysaccharide polymers, without the viscosity increasing beyond 30 cp (centipoises) or beyond 25 cP at 20° C. and using no surfactants. Viscosity is preferably measured at 20° C. and remain less than 30 cP or less than 20 cP, or is comprised between 18-30 cP, and is stable over time during long periods of storage of the compositions, up to 18 months or up to 36 months as shown in the Examples.

It is remarkable to observe that the stability of the suspensions obtained according to the present invention does not require any particular actions during their preparation and in particular does not require any significant shearing for the formation of a three-dimensional structure.

The suspension according to the present invention is obtained by dissolution of the ingredients successively with stirring, starting by dissolving the polysaccharide which may require slight heating of the solubilisation medium (40° C. for example). The solubilisation of these polymer compounds may take around 1 to 2 hrs, and may be accelerated if the powder is slowly poured into the solubilisation medium stirred sufficiently in order to form a major vortex. The formation of clumps of powder which are subsequently hard to dissolve may then be avoided. The addition of various ingredients (e.g. buffer, etc.) may be performed at the beginning or the end of the operations. The addition of micronized active substance and possibly micronized metallic oxide is performed at ambient temperature with vigorous stirring (vortex) in order to avoid formation of clumps or lumps. It may also be advantageous in order to accelerate formation of the suspension and guarantee good homogeneity of the mixture to perform deflocculation of the suspension using a colloidal mill, under vacuum if necessary, which has the additional advantage of avoiding trapping air bubbles. Deflocculation is performed with a rapid stirrer equipped with a deflocculating impeller, but it is not necessary to use a system of the rotor/stator type which induces major local shear that may be harmful to the integrity of the polymers. A simple homogenisation of the micronized powder of silicon oxide at about 300 rpm is performed. As demonstrated in the Examples below, suspensions that are produced on an industrial scale of about 4,000 L require the application of a shear force of 3,000 rpm for the incorporation of the polysaccharides according to the invention, such as xanthan gum, but this step is performed before the dispersion of the micronized powder of silicon oxide which are always homogenized using regular shear of 300 rpm.

Owing to the low level of viscosity, the suspension according to the present invention can be easily administered with a precise dosage, obtained with a dropper or dispensing syringe for example. Since the suspension has very good homogeneity and a low level of viscosity and no excessive wettability of the walls of the container or syringe, dosage is particularly easy and precise. Furthermore, the absence of surfactants such as lauryl sulphate or polysorbates avoids any foaming phenomena, both during manufacture and use. It is not therefore necessary to add any anti-foaming compound, such as simethicone derivatives, which is an additional advantage of the invention.

According to a third aspect, the present invention relates to a delivery system of precise and determined quantities of the suspensions according to the present invention. Such delivery systems may have the form of a dropper, a pump, a syringe, a pipette, or any other delivery device capable of delivering a determined volume of the suspension according to the present invention.

Such delivery systems may be mechanically, automatically, or electronically operated, or may be programmed. They may also be based on any other type of operation well known in the art. The delivery devices or systems according to the present invention allow delivering precise dosages of oral suspensions in a convenient, fast and reproducible manner.

EXAMPLES

Example 1

Meloxicam Suspension Containing Carboxymethyl Cellulose

In one embodiment, a meloxicam suspension comprising the ingredients as listed in Table 1 below was prepared.

TABLE 1

| Ingredients | % weight/volume |
| --- | --- |
| Meloxicam | 0.15 |
| Sodium carboxymethylcellulose | 0.35 |
| Silicon dioxide (Aerosil 200) | 2 |
| Sorbitol (aqueous solution 70%) | 30 |
| Glycerol | 15 |
| Xylitol | 15 |
| Sodium benzoate | 0.15 |
| Citric acid | 0.15 |
| Demineralised water | to 100 |

After one week of storage on a vibrating table, two separate phases appear in the suspension.

Example 2

Meloxicam Suspension Stabilised Containing Xanthan Gum

In another embodiment, a meloxicam suspension comprising the ingredients as listed in Table 2 below was prepared.

TABLE 2

| Ingredients | % weight/volume |
| --- | --- |
| Meloxicam | 0.15 |
| Xanthan gum | 0.25 |
| Silicon dioxide (Aerosil 200) | 2 |
| Sorbitol (aqueous solution 70%) | 30 |
| Glycerol | 15 |
| Xylitol | 15 |
| Sodium benzoate | 0.15 |
| Citric acid | 0.1 |
| Demineralised water | to 100 |

The suspensions as listed in Table 1 and 2 were obtained by a manufacturing process comprising the following steps 1 to 5:

Step 1: sodium benzoate and xylitol were added to a mixture of glycerol, sorbitol and water, mixing at 300 rpm for 10 min using a helicoidal mixer;

Step 2: the mixture obtained was subsequently heated to 30° C. and sodium carboxymethylcellulose (CMC) or xanthan gum was gently added with stirring at 300 rpm using a helicoidal mixer and was homogenised with a deflocculating blade for 30 min;

Step 3: citric acid was added after homogenisation of the carboxymethylcellulose or xanthan gum;

Step 4: meloxicam and silicon dioxide were subsequently added with stirring at 300 rpm using a helicoidal mixer for 30 min, followed with a deflocculating blade for 10 minutes;

Step 5: the initial volume of the suspension was adjusted and mixed for 30 minutes; and Step 6: the suspension was adjusted to a volume of 300 mL with demineralised water and was homogenised for 10 minutes at 3,000 rpm;

Long-term stability studies showed that the suspension comprising the ingredients as listed in Table 2 did not show any phase separation after one week of storage when placed on a vibration table system and remained stable over several months, up to 36 months at 20° C. when stored in vials.

Example 3

Stability Studies

Three batches of meloxicam suspension as described in Example 2 have been tested as to their stability over long periods of time when stored in vials. Results are provided in Table 3 below.

TABLE 3

|  | T0 | | T18 months | | T36 months | |
| --- | --- | --- | --- | --- | --- | --- |
|  | Viscosity at 20° C. | Appearence | Viscosity at 20° C. | Appearence | Viscosity at 20° C. | Appearence |
| Batch P02 | 23.0 cP | Homogeneous suspension - no phase separation | 27.4 cP | Homogeneous suspension - no phase separation | 18.3 cP | Homogeneous suspension - no phase separation |
| Batch P03 | 21.5 cP | Homogeneous suspension - no phase separation | 27.8 cP | Homogeneous suspension - no phase separation | 18.0 cP | Homogeneous suspension - no phase separation |
| Batch P04 | 19.8 cP | Homogeneous suspension - no phase separation | 25.7 cP | Homogeneous suspension - no phase separation | 22.3 cP | Homogeneous suspension - no phase separation |

Results as displayed in Table 3 clearly show that meloxicam compositions according to the present invention had excellent stability characteristics during long periods of storage of up to 18 months and 36 months without any phase separation. They also maintained a very good homogeneous aspect during the whole storage period at 20° C.

Example 4

Stabilized Suspensions of Meloxicam

Suspensions of meloxicam comprising ingredients such as those listed in Table 4 below were prepared.

TABLE 4

| Ingredients | % weight/ volume | % weight/ Volume | % weight/ Volume | % weight/ Volume | % weight/ volume |
| --- | --- | --- | --- | --- | --- |
| Meloxicam | 0.25 | 0.5 | 0.75 | 0.25 | 0.25 |
| Xanthan gum | 0.25 | 0.25 | 0.25 | 0.4 | 0.4 |
| Silicon dioxide (Aerosil 200) | 2 | 2 | 2 | 2 | 1.5 |
| Sorbitol (aqueous solution 70%) | 30 | 30 | 30 | 30 | 30 |
| Glycerol | 15 | 15 | 15 | 15 | 15 |
| Xylitol | 15 | 15 | 15 | 15 | 15 |
| Sodium benzoate | 0.15 | 0.15 | 0.15 | 0.5 | 0.15 |
| Citric acid | 0.1 | 0.1 | 0.1 | 0.1 | 0.1 |
| Demineralised water | to 100 | to 100 | to 100 | to 100 | to 100 |

The suspensions as described in Table 4 are obtained using the process of preparation having the following steps 1-6:

Step 1: sodium benzoate and xylitol are added to a mixture of glycerol, sorbitol and water, mixing at 300 rpm for 10 min using a helicoidal mixer;

Step 2: the mixture obtained is subsequently heated to 30° C. and xanthan gum is gently added with stirring at 300 rpm using a helicoidal mixer and is homogenised with a deflocculating blade for 30 min;

Step 3: citric acid is added after homogenisation of xanthan gum;

Step 4: meloxicam and silicon dioxide are subsequently added with stirring at 300 rpm using a helicoidal mixer for 30 min, followed with a deflocculating blade for 10 minutes;

Step 5: the initial volume of the suspension is adjusted and mixed for 30 minutes; and Step 6: the suspension is adjusted to a volume of 300 mL with demineralised water and is homogenised for 10 minutes at 3,000 rpm.

Example 5

Stabilized Suspensions of Meloxicam

The suspensions of meloxicam comprising ingredients such as those listed in Table 5 below were prepared.

TABLE 5

| Ingredients | % weight/ volume | Ingredients | % weight/ volume |
| --- | --- | --- | --- |
| Meloxicam | 0.15 | Meloxicam | 0.15 |
| Xanthan gum | 0.25 | Xanthan gum | 0.25 |
| Aluminium oxide | 2 | Titanium oxide | 2 |
| Sorbitol (aqueous solution 70%) | 30 | Sorbitol (aqueous solution 70%) | 30 |
| Glycerol | 15 | Glycerol | 15 |
| Xylitol | 15 | Xylitol | 15 |
| Sodium benzoate | 0.15 | Sodium benzoate | 0.15 |
| Citric acid | 0.1 | Citric acid | 0.1 |
| Demineralised water | to 100 | Demineralised water | to 100 |

The suspensions as described in Table 5 are obtained using the process of preparation consisting of the following steps 1-6:

Step 1: sodium benzoate and xylitol are added to a mixture of glycerol, sorbitol and water, mixing at 300 rpm for 10 min using a helicoidal mixer;

Step 2: the mixture obtained is subsequently heated to 30° C. and xanthan gum is gently added with stirring at 300 rpm using a helicoidal mixer and is homogenised with a deflocculating blade for 30 min;

Step 3: citric acid is added after homogenisation of xanthan gum;

Step 4: meloxicam and aluminium oxide or titanium oxide are subsequently added with stirring at 300 rpm using a helicoidal mixer for 30 min, followed with a deflocculating blade for 10 minutes;

Step 5: the initial volume of the suspension is adjusted and mixed for 30 minutes; and Step 6: the suspension is adjusted to a volume of 300 mL with demineralised water and is homogenised for 10 minutes at 3,000 rpm.

Example 6

Preparation of Batches of Suspensions of Meloxicam on an Industrial Scale of 4,000 L Industrial suspensions batches of 4,000 L are prepared with ingredients as listed in the following Table 6.

| Ingredients | % weight/volume |
|---|---|
| Meloxicam | 0.15 |
| Xanthan gum | 0.25 |
| Silicon dioxide (Aerosil 200) | 2 |
| Sorbitol (aqueous solution 70%) | 30 |
| Glycerol | 15 |
| Xylitol | 15 |
| Sodium benzoate | 0.15 |
| Citric acid | 0.15 |
| Demineralised water | to 100 |

Industrial batches suspensions as listed in Table 6 are obtained using the process of preparation consisting of the following steps 1-6:

Step 1: sodium benzoate and xylitol are added to a mixture of glycerol, sorbitol and water, mixing at 300 rpm for 10 min using a helicoidal mixer;

Step 2: the mixture obtained is subsequently heated to 30° C. and xanthan gum is gently added with stirring at 3000 rpm using a helicoidal mixer and is homogenised with a deflocculating blade for 30 min;

Step 3: citric acid is added after homogenisation of xanthan gum;

Step 4: meloxicam and silicon dioxide are subsequently added with stirring at 300 rpm using a helicoidal mixer with a deflocculating blade for 10 minutes;

Step 5: the initial volume of the suspension is adjusted and mixed for 30 minutes; and Step 6: the suspension is adjusted to a volume of 4000 L with demineralised water and is homogenised for 10 minutes at 3,000 rpm.

For the preparation of industrial batches of suspensions of 4,000 L, xanthan gum is incorporated with a shear force of 3,000 rpm, however the silicon dioxide itself is incorporated by simple mixing at 300 rpm so that the three-dimensional structure is not modified.

The invention claimed is:

1. A pharmaceutical composition intended for administration via the oral route, comprising a suspension of a micronized powder of meloxicam, or salts thereof, as a sole active ingredient, dispersed in a physiological medium comprising about 0.01 to 1% by mass of a polysaccharide polymer selected from the group consisting of carrageenans, xanthans, guars and alginic acid derivatives, and 0.1 to 2% by mass of a micronized powder of silicon oxide, wherein the pharmaceutical substance has a solubility of less than 500 mg/L in the dispersion medium at ambient temperature, and wherein the composition does not comprise any derivatives of cellulose ethers.

2. The pharmaceutical composition according to claim 1, wherein the viscosity of the suspension is less than 30 centipoise (cP) at 20° C.

3. The pharmaceutical composition according to claim 1, further comprising 50 to 70% of a mixture of polyols.

4. The pharmaceutical composition according to claim 1 wherein the polysaccharide is a xanthan gum.

5. The pharmaceutical composition according to claim 1, wherein meloxicam or salts thereof is micronized and has a unimodal size profile centered on a mean value of less than 10 μm.

6. The pharmaceutical composition according to claim 1 wherein the meloxicam proportion is from 0.05 to 1% by mass.

7. The pharmaceutical composition according to claim 1, wherein the dispersion medium comprises an aqueous buffer, and the composition has a pH between 2 and 4.

8. The pharmaceutical composition according to claim 1, said composition further comprising a mixture of polyols selected from the group consisting of glycerol, mannitol, sorbitol and xylitol.

9. The pharmaceutical composition according to claim 1, said composition further comprising a sweetener or an antimicrobial preservative.

10. The pharmaceutical composition according to claim 1, wherein the composition does not comprise any additional flavouring agent.

11. A process for preparing a stable aqueous suspension of micronized powder of claim 1, comprising the step of adding between 0.01 and 1% of a polysaccharide polymer selected from the group consisting of carrageenans, xanthans, guars, and alginic acid derivatives, and 0.1 to 2% by mass of micronized powder of silicone oxide to meloxicam or salts thereof in suspension in a dispersion physiological medium.

12. The pharmaceutical composition according to claim 1, wherein the meloxicam proportion is from 0.05% to 0.15% by mass.

* * * * *